United States Patent [19]

Bundy

[11] 4,093,813
[45] June 6, 1978

[54] INTER-OXA-13,14-DIHYDRO-9-DEOXY-PGF COMPOUNDS

[75] Inventor: Gordon L. Bundy, Portage, Mich.

[73] Assignee: The Upjohn Company, Kalamazoo, Mich.

[21] Appl. No.: 786,713

[22] Filed: Apr. 11, 1977

Related U.S. Application Data

[62] Division of Ser. No. 614,243, Sep. 17, 1975, Pat. No. 4,033,989.

[51] Int. Cl.² ............................................. C07C 177/00
[52] U.S. Cl. .................................. 560/121; 260/514 D
[58] Field of Search ..................... 560/121; 260/514 D

[56] References Cited

U.S. PATENT DOCUMENTS 3,678,092   7/1972   Finch ..................................... 560/121

FOREIGN PATENT DOCUMENTS 767,704   11/1971   Belgium ............................... 560/121

Primary Examiner—Paul J. Killos
Attorney, Agent, or Firm—Robert A. Armitage

[57] ABSTRACT

Prostaglandin analogs with the following cyclopentane ring structure:

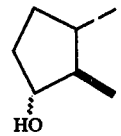

are disclosed along with intermediates useful in their preparation and processes for their preparation. These analogs are useful for some of the same pharmacological purposes as the prostaglandins.

25 Claims, No Drawings

INTER-OXA-13,14-DIHYDRO-9-DEOXY-PGF COMPOUNDS

The present application is a divisional application of Ser. No. 614,243, filed Sep. 17, 1975, now issued as U.S. Pat. No. 4,033,989 on Jul. 5, 1977.

The present invention relates to prostaglandin analogs for which the essential material constituting a disclosure therefor is incorporated by reference here from U.S. Pat. No. 4,033,989, issued Jul. 5, 1977.

I claim:

1. A prostaglandin analog of the formula

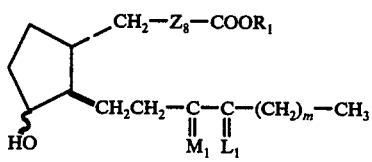

wherein $m$ is one to 5, inclusive;
wherein $M_1$ is

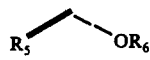

or

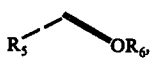

wherein $R_5$ and $R_6$ are hydrogen or methyl, with the proviso that one of $R_5$ and $R_6$ is methyl only when the other is hydrogen;
wherein $L_1$ is

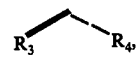

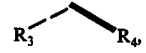

or a mixture of

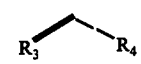

and

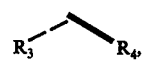

wherein $R_3$ and $R_4$ are hydrogen, methyl, or fluoro, being the same or different, with the proviso that one of $R_3$ and $R_4$ is fluoro only when the other is hydrogen or fluoro;
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation; and
wherein $Z_8$ is
(1) —$CH_2$—O—$CH_2$—$(CH_2)_g$—$CH_2$—,
(2) —$(CH_2)_2$—O—$(CH_2)_g$—$CH_2$—, or
(3) —$(CH_2)_3$—O—$(CH_2)_g$—,
wherein $g$ is one, 2, or 3.

2. A compound according to claim 1, wherein $M_1$ is

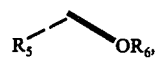

3. A compound according to claim 1, wherein $M_1$ is

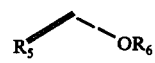

4. A compound according to claim 3, wherein $m$ is 3.
5. A compound according to claim 4, wherein $Z_8$ is

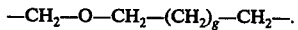

6. A compound according to claim 5, wherein $g$ is 3.
7. A compound according to claim 5, wherein $g$ is one.
8. A compound according to claim 7, wherein $R_5$ and $R_6$ are both hydrogen.
9. A compound according to claim 8, wherein $R_3$ and $R_4$ are both hydrogen.
10. 5-Oxa-13,14-dihydro-9-deoxy-PGF$_1$, a compound according to claim 9.
11. A compound according to claim 8, wherein $R_3$ and $R_4$ are both fluoro.
12. 16,16-Difluoro-5-oxa-13,14-dihydro-9-deoxy-PGF$_1$, a compound according to claim 8.
13. A compound according to claim 5, wherein $Z_8$ is

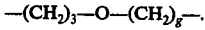

14. A compound according to claim 13, wherein $g$ is 3.
15. A compound according to claim 14, wherein $R_5$ and $R_6$ are both hydrogen.
16. A compound according to claim 15, wherein $R_3$ and $R_4$ are both hydrogen.
17. 2a,2b-Dihomo-3-oxa-13,14-dihydro-9-deoxy-PGF$_1$, a compound according to claim 16.
18. A compound according to claim 15, wherein $R_3$ and $R_4$ are both fluoro.
19. 2a,2b-Dihomo-16,16-difluoro-3-oxa-13,14-dihydro-9-deoxy-PGF$_1$, a compound according to claim 18.
20. A compound according to claim 13, wherein $g$ is one.
21. A compound according to claim 20, wherein $R_5$ and $R_6$ are both hydrogen.
22. A compound according to claim 21, wherein $R_3$ and $R_4$ are both hydrogen.
23. 3-Oxa-13,14-dihydro-9-deoxy-PGF$_1$, a compound according to claim 22.
24. A compound according to claim 21, wherein $R_3$ and $R_4$ are both fluoro.
25. 16,16-Difluoro-3-oxa-13,14-dihydro-9-deoxy-PGF$_1$, a compound according to claim 24.

* * * * *